United States Patent [19]
Hubbard et al.

[11] Patent Number: 4,481,216
[45] Date of Patent: Nov. 6, 1984

[54] CONTROL OF CORN ROOTWORM BY APPLICATION OF N-METHYL 2-(1-METHYLETHYL)PHENYLCARBAMATE

[75] Inventors: Winchester L. Hubbard, Woodbridge; Richard C. Moore, Wallingford, both of Conn.

[73] Assignee: Uniroyal, Inc., New York, N.Y.

[21] Appl. No.: 540,571

[22] Filed: Oct. 7, 1983

[51] Int. Cl.³ ............................................. A01N 47/10
[52] U.S. Cl. ..................................... 424/300; 424/286
[58] Field of Search ................................ 424/286, 300

[56] References Cited

U.S. PATENT DOCUMENTS

| | | | |
|---|---|---|---|
| 3,215,595 | 11/1965 | Bocker et al. | 424/300 |
| 3,250,673 | 5/1966 | Bagley | 424/300 |
| 4,065,558 | 12/1977 | Gordon | 424/216 |
| 4,067,990 | 1/1978 | Dulat et al. | 424/300 |
| 4,324,781 | 4/1982 | Okamoto et al. | 424/300 |

*Primary Examiner*—Leonard Schenkman
*Assistant Examiner*—F. Abramson
*Attorney, Agent, or Firm*—Marvin Bressler

[57] ABSTRACT

A method is disclosed for combating the soil insect, corn rootworm which comprises contacting the corn rootworm with an effective amount of N-methyl 2-(1-methylethyl)phenylcarbamate.

2 Claims, No Drawings

CONTROL OF CORN ROOTWORM BY APPLICATION OF N-METHYL 2-(1-METHYLETHYL)PHENYLCARBAMATE

REFERENCE TO RELATED APPLICATION

This a continuation-in-part of U.S. patent application, Ser. No. 417,009, filed Sept. 13, 1982 now abandoned.

BACKGROUND OF THE INVENTION

1. Field of the Invention

The instant invention is directed to a method of controlling corn rootworm. Most particularly, the instant invention is directed to a method for combating corn rootworm with an effective amount of N-methyl 2-(1-methylethyl)phenylcarbamate.

2. Description of the Prior Art

Corn rootworms are the larvae of several species of beetles of the genus Diabrotica. These larvae cause severe damage to the roots of corn plants, particularly in fields where one corn crop follows another in successive seasons. The adult beetles lay their eggs in the soil of a maturing crop corn. The eggs lay dormant in the soil until the following spring. Then they hatch in response to favorable soil temperatures and the larvae feed on the roots of young corn plants causing reduction in yield and/or the stalks to topple over when subjected to either wind or wet soil conditions. The fallen stalks cannot be satisfactorily harvested by mechanical harvesters causing significant losses.

One method of combating corn rootworm, known in the prior art, is to apply an insecticidally effective amount of N-methyl 3-(1-methylethyl)phenylcarbamate to the soil around which the corn is planted. This method is disclosed in U.S. Pat. No. 3,250,673, May 10, 1966 (Bagley). It is noted that this reference refers to this compound as 3-isopropylphenyl N-methylcarbamate or meta-isopropylphenyl N-methylcarbamate (herein called MIC). This compound is recited, in the patent, to be effective, against corn rootworm. The reference further teaches the application of the MIC months after planting of seeds, that is, MIC application is a task separate from planting and at a time when the eggs have hatched and the corn has already grown. One of ordinary skill in the art will realize that treating a field of corn that has attained considerable growth is a difficult and time consuming undertaking and may do physical damage to the already existing corn plants. Application rates of from 2-4 lbs/a (2.24-4.48 kg/a) are also mentioned.

The ortho-isomer of MIC is N-methyl 2-(1-methylethyl)phenylcarbamate (herein called OIC) a known foliar insecticide. This insecticide, applied directly to plants, is commercially used in the protection of rice crops. However, OIC has never been known to be effective in the control of soil insects. That is, OIC has never been suggested to be used as a soil insecticide.

SUMMARY OF THE INVENTION

It has now veen unexpectedly found that N-methyl 2-(1-methylethyl)phenylcarbamate (OIC) provides long lasting effective control of corn rootworm residing in the soil wherein corn is planted.

This invention provides several advantages over known methods especially over that taught by Bagley, namely, the compound of this invention has superior resistance to degradation caused by the influences of a soil environment. OIC can be applied simultaneously with planting of the corn seed, and the one initial application is usually sufficient for the planting season. OIC may be added to the soil at relatively low rates while still exerting effective control of corn rootwormm over extended period of time, whereas MOC at the same application rate is ineffective over long periods of time.

The compound of this invention may be applied to the soil for the purpose of contacting corn rootworm in forms well known to the art such as a solution in a suitable solvent such as aliphatic alcohols, aliphatic ketones, and the like, or as a wettable powder or an emulsifiable concentrate. Dust and granular forms of OIC may also be employed; a granular form is usually preferred. In the latter case, OIC is dissolved in a solvent and sprayed onto an inert mineral carrier such as attapulgite granules (10-100 mesh), and the solvent is then evaporated. Such granular compositions may contain from 2-25% OIC based on the carrier plus OIC, usually 3-15%. In addtion, the pesticide may also be incorporated into a polymeric carrier such as polyethylene, polypropylene, butadiene-styrene, styrene-acrylonitrile resins, polyamides, poly(vinyl acetates) and the like. When encapsulated the OIC may advantageously be released over an even longer time period, extending its effectiveness further than when used in non-encapsulated form.

DETAILED DESCRIPTION

In order to carry out this invention, OIC is applied to the soil at a rate of from 0.25-12 lbs./a (0.28-13.4 kg/ha). However, it should be considered that in so-called "band" applications, i.e., when OIC is placed on or into the soil along with seeds as a band approximately 2-8 inches (5-20 cm) on each side of the row of seeds, lower rates such as 0.25-3 lbs/a (0.28-3.4 kg/ha) may suffice to control corn rootworm. When the compound of this invention is spread in a so-called "broadcast" fashion, larger doses may be required, such as 1-12 lbs/a (1.12-13.4 kg/ha). Usually, 0.5-8 lbs/a (ca 0.6-10.1 kg/ha) of OIC is needed, i.e., 0.5-2 lbs/a (0.6-2.24 kg/ha) for band application and about 2-9 lbs/a (7.8-10 kg/ha) for broadcast use.

It is also within the contemplation of this invention that the OIC be added to the soil in combination with other pesticides, as well as plant nutrients, fertilizers and the like.

EXAMPLE 1

Dispersions were prepared having concentrations of 5, 10, 20, 40 and 80 ppm of OIC by adding the required amount of water to a mixture of 100 parts acetone, 6 parts of OIC and 3 parts of surface active agent (Emulfor [trademark] EL719, polyoxyethylated vegetable oil). Similarly, dispersions of MIC having the above mentioned concentrations were prepared in the same manner.

Flower pots having a 3.5 inch (8.9 cm) diameter were each filled with 360 g of dry soil and 40 ml of the above dispersions were added to the pots resulting in a concentration of the active ingredient in the soil of 0.5, 1.0, 2.0, 4.0 and 8.0 ppm. The following planting, infestation and evaluation schedule was employed.

| Test | Time from Addition of OIC OR MIC | | Scoring |
|---|---|---|---|
| | Planting | Infestation[3] | |
| 1 week | Immediately[1] | 1 week | 2 weeks |

-continued

| Test | Time from Addition of OIC OR MIC | | |
|------|----------|--------------|---------|
|      | Planting | Infestation[3] | Scoring |
| 4 weeks | 3 weeks[2] | 4 weeks | 5 weeks |
| 6 weeks | 5 weeks[2] | 6 weeks | 7 weeks |

Remarks:
[1]Two seeds of sweet corn variety "Silver Queen."
[2]Two seeds of sweet corn variety "Pioneer Hibrid."
[3]Ten third instar larvae of Southern corn rootworm *Diaprotica undecimpunctata howardi*.

All experiments were conducted with 6 replicates each, including controls which had not been treated with OIC or MIC.

Scoring was undertaken by emptying the pots of their soil, filtering the soil through a fine mesh screen and retaining the larvae present. The number of live larvae was counted, and percent control of Southern corn rootworm was calculated using Abbot's formula (see J. Economic Entomology 18, 265-267 (1925)).

The results of the experiments are summarized in Table I.

TABLE I

| Test | 1 Week | | 4 Weeks | | 6 Weeks | |
|------|--------|------|---------|------|---------|------|
| Compound | OIC | MIC* | OIC | MIC* | OIC | MIC* |
| % Control** | | | | | | |
| at 8 ppm | — | — | 100 | 24 | 93.3 | 0 |
| 4 | 100 | 88 | 97.5 | 11 | 73 | 0 |
| 2 | 100 | 95.3 | 100 | 4 | 26 | 0 |
| 1 | 95.3 | 100 | 57 | 0 | 37 | 0 |
| 0.5 | 79 | 97.7 | — | — | — | — |

*Outside this invention.
**All replicates not including OIC or MIC indicated zero percent control of corn rootworm.

The above results clearly indicate the unexpectedly superior long range efficacy, i.e., after four weeks or more after insecticidal treatment, of OIC (N-methyl 2-(1-methylethyl)phenylcarbamate) over MIC (N-methyl 3-(1-methylethyl)phenylcarbamate) in controlling corn rootworm.

EXAMPLE 2

OIC was dissolved in acetone. The solution was admixed with attapulgus clay, an ineret carrier, to form a slurry. The slurry was heated with the resultant evaporation of the acetone solvent and the absorption of the OIC onto the clay. The clay particles were found to contain 4% by weight of absorbed OIC, based on the total weight of the particles.

The 4% OIC clay particles were evenly distributed over a plot 10 feet long by 6 inches wide upon which nine newly transplanted cabbage plants were evenly spaced such that the application rate was equal to 1 pound of OIC per acre. In a second run the 4% clay particle application rate was increased such that the effective rate was equal to 2 pounds of OIC per acre. Each run was duplicated.

The cabbage plants were allowed to grow for 71 days at which time they were dug up and their root structure evaluated. Based on the standard test evaluation methods it was determined that OIC, at both 1 and 2 pound per acre application rates, was ineffective at protecting the roots of the cabbage plants from attack of the soil insect, *Hylemya brassicae*, commonly known as cabbage maggot.

EXAMPLE 3

Dispersions having concentrations of 100 and 1,000 ppm OIC were prepared in accordance with the procedure of Example 1. Larvae of black cutworm, *Agrotis ipsison*, a well known soil insect, were sprayed, in separate tests, with the 100 and 1,000 ppm OIC dispersions. This treatment was ineffective at controlling the larvae.

As stated above, although OIC is a known foliar insecticide, it has never been shown to be effective against woil insects. This is consistent with results obtained by other investigators in their experiences using other foliar insecticides applied against insects residing in the soil. (See U.S. Pat. No. 4,065,558). Examples 2 and 3 confirm the fact that OIC is ineffective against two well known soil insects. Thus, it is all the more remarkable and unexpected that OIC not only provides effective control of the soil insect, corn rootworm, but does so over long periods of time.

The above preferred embodiment and examples will make apparent to those skilled in the art other embodiments and examples within the scope of the instant invention. These other embodiments and examples, suggested by the scope and spirit of the instant invention, are within the contemplation of this invention. The invention, therefore, should be limited only by the appended claims.

What is claimed is:

1. A method for controlling corn rootworm by contacting said corn rootworm with at least 1 ppm of N-methyl 2-(1-methylethyl)phenylcarbamate.

2. A method in accordance with claim 1 wherein said contact is provided by applying said N-methyl 2-(1-methylethyl)phenylcarbamate to the soil.

* * * * *